(12) United States Patent
Ahong et al.

(10) Patent No.: US 11,419,771 B2
(45) Date of Patent: Aug. 23, 2022

(54) HYGIENE MONITORING SYSTEM

(71) Applicant: Essity Hygiene and Health Aktiebolag, Gothenburg (SE)

(72) Inventors: Timothy Ahong, Mississauga (CA); Shyam Mali, Etobicoke (CA); Danny Porthiyas, Toronto (CA); Joel Ironstone, Toronto (CA); Jacob Edding, Mississauga (CA); Martin Rozee, Toronto (CA)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 304 days.

(21) Appl. No.: 16/757,500

(22) PCT Filed: Nov. 17, 2017

(86) PCT No.: PCT/EP2017/079673
§ 371 (c)(1),
(2) Date: Apr. 20, 2020

(87) PCT Pub. No.: WO2019/096412
PCT Pub. Date: May 23, 2019

(65) Prior Publication Data
US 2021/0361493 A1 Nov. 25, 2021

(51) Int. Cl.
*A61F 13/42* (2006.01)
*A61B 5/1477* (2006.01)
(Continued)

(52) U.S. Cl.
CPC ........... *A61F 13/42* (2013.01); *A61B 5/0002* (2013.01); *A61B 5/1477* (2013.01);
(Continued)

(58) Field of Classification Search
USPC ...................................................... 340/573.1
See application file for complete search history.

(56) References Cited

U.S. PATENT DOCUMENTS 5,686,902 A 11/1997 Reis et al.
2011/0254682 A1* 10/2011 Sigrist Christensen .................... G16H 40/20
340/539.12

(Continued)

FOREIGN PATENT DOCUMENTS

CN 103547926 A 1/2014
JP 2011147505 A 8/2011
(Continued)

OTHER PUBLICATIONS

National Intellectual Property Administration (CNIPA) of the People's Republic of China, Notification of the First Office Action, Application No. 201780096735.0, dated Sep. 21, 2020 (15 pages).
(Continued)

*Primary Examiner* — Kerri L McNally
(74) *Attorney, Agent, or Firm* — Cantor Colburn LLP

(57) ABSTRACT

A hygiene monitoring system comprising: a hygiene monitoring device, the hygiene monitoring device comprising a housing with an identifier-obtaining component; and a station for receiving the hygiene monitoring device, the station comprising: a securing component configured to receive and hold the housing at a defined location relative to the station; and a station identifier configured to provide an identifier to the identifier-obtaining component when the housing of the hygiene monitoring device is received by the securing component of the station.

22 Claims, 11 Drawing Sheets

(51) Int. Cl.
*A61B 5/00* (2006.01)
*A61B 90/90* (2016.01)

(52) U.S. Cl.
CPC ............ *A61B 5/6808* (2013.01); *A61B 90/90* (2016.02); *A61F 2013/424* (2013.01)

(56) References Cited

U.S. PATENT DOCUMENTS

| | | | | |
|---|---|---|---|---|
| 2012/0274468 | A1* | 11/2012 | Wegelin | A61L 2/24 340/573.1 |
| 2013/0012896 | A1* | 1/2013 | Suzuki | G16H 40/63 604/361 |
| 2014/0320289 | A1* | 10/2014 | Raichman | G16H 40/67 340/573.1 |
| 2015/0235549 | A1* | 8/2015 | Limbert | E05B 35/002 222/173 |
| 2016/0134497 | A1* | 5/2016 | Oloffson Ranta | H04W 84/12 709/219 |

FOREIGN PATENT DOCUMENTS

| | | |
|---|---|---|
| JP | 2012502343 A | 1/2012 |
| JP | 2016524131 A | 8/2016 |
| JP | 2016170070 A | 9/2016 |
| JP | 2017000707 A | 1/2017 |
| WO | 2016090492 A1 | 6/2016 |
| WO | 2016190008 A1 | 12/2016 |

OTHER PUBLICATIONS

Journal of Practical Electrocardiology, Remote ECG Monitoring Technology, vol. 25, No. 2, Apr. 2016 (4 pages).

Rim Negra et al. / Procedia Computer Science, Wireless Body Area Networks: Applications and technologies, 83 (2016) 1274-1281 (8 pages).

China National Intellectual Property Administration, Notice Of Granting Patent Right For Invention, Application No. 201780096735.0, dated Apr. 8, 2021 (8 pages).

Japanese Patent Office, Notice of Allowance, Application No. 2020-527056, dated Oct. 25, 2021 (3 pages).

Japanese Patent Office, Notice of Reasons for Rejection, Application No. 2020-527056, dated Jul. 5, 2021 (8 pages).

European Patent Office, International Search Report and Written Opinion of the International Searching Authority, International Application No. PCT/EP2017/079673, dated Aug. 9, 2018 (12 pages).

\* cited by examiner

HYGIENE MONITORING SYSTEM

CROSS-REFERENCE TO RELATED APPLICATION

The present application is a national stage entry under 35 U.S.C. § 371 of, and claims priority to, International Application No. PCT/EP2017/079673, filed Nov. 17, 2017, the disclosure of which is hereby incorporated herein by reference in its entirety.

FIELD OF THE INVENTION

The present disclosure relates to a hygiene monitoring system, and, in particular, a hygiene monitoring system comprising a hygiene monitoring device and a station for receiving the hygiene monitoring device.

BACKGROUND OF THE INVENTION

A hygiene monitoring device may be used to monitor a hygienic state of a user. For example, a hygiene monitoring device may monitor a wetness level, a temperature and/or a concentration of a particular substance associated with the user. In certain situations, the hygiene monitoring device may be attached to an article which is worn by the user. For example, the hygiene monitoring device may monitor the saturation level and/or distribution of liquid with a disposable absorbent hygiene article, e.g., a diaper, incontinence shield or sanitary napkin. Typically, the hygiene monitoring device transmits information relating to the monitored hygienic state of the user, such as a soiling event.

In residences, such as care homes, hospitals and the like, where residents are under the care of caregivers, several hygiene monitoring devices may be interchangeably used with several different residents (for example, the hygiene monitoring devices may be used with different residents during different periods, such as different days). In certain devices, the hygiene monitoring device may alert a caregiver when it detects a change in the hygienic state of a user, such as a soiling event. In such cases, the hygiene monitoring device may communicate the information relating to the monitored hygienic state of the resident to a common, centralised monitoring system which is configured to alert a caregiver of a change in the hygienic state. The centralised monitoring system alerts the caregiver as to which resident needs attention so that the caregiver may attend to this resident.

Accordingly, during every period, the data being received by the centralised monitoring system from each of the hygiene monitoring devices must be associated with one particular resident such that the centralised monitoring system may notify the caregiver which resident needs tending to. To this end, typically, each hygiene monitoring device has a unique serial number which is transmitted to the centralised monitoring system along with the information relating to the hygienic state.

However, in such systems, the caregiver provides the centralised monitoring system with a mapping of which serial number (corresponding to a hygiene monitoring device) is associated with which resident.

As care homes tend to be busy places and hygiene monitoring devices are often switched between residents, e.g., to replace faulty units or to recondition (e.g., clean) used units, or as residents in the care home leave or move, e.g., due to hospital admission, it has been found that caregivers may either forget or inaccurately assign (or re-assign) the hygiene monitoring device to the correct residents.

Accordingly, there is a need for an improved hygiene monitoring system which allows for an association between recorded data from a hygiene monitoring device and the user to be conveniently and reliably maintained.

SUMMARY OF THE INVENTION

According to an aspect of the present disclosure, there is provided a hygiene monitoring system comprising a hygiene monitoring device, the hygiene monitoring device comprising a housing with an identifier-obtaining component; and a station for receiving the hygiene monitoring device, the station comprising a securing component configured to receive and hold the housing at a defined location relative to the station; and a station identifier configured to provide an identifier to the identifier-obtaining component when the housing of the hygiene monitoring device is received by the securing component of the station.

With the above system, the station may be placed or installed within the care home (permanently or semi-permanently) so that it is associated with a resident and/or a spatial location unique for that resident, for example, by placing or installing it next to their bed. Accordingly, the caregiver may conveniently place the hygiene monitoring device in the station regularly before/after its use. As the station identifier is associated with the particular bed (which is in turn associated with a particular patient), upon the identifier-obtaining component receiving the identifier, the hygiene monitoring device may store and transmit the identifier which is associated with the identifier station, which, in turn is associated with a bed, which, in turn is associated with a particular resident. It has been observed that residents change beds much less often than monitoring devices need to be reassigned between residents.

If the hygiene monitoring device is to be used with a new resident, the caregiver naturally places it in the station associated with the spatial location unique for the new resident (such as a station next to their bed), thereby conveniently and reliably receiving a new identifier by the hygiene monitoring device.

Hence, with such a configuration, it is possible to provide an improved hygiene monitoring system which allows for an association between recorded data from a hygiene monitoring device and the resident to be conveniently and reliably maintained.

In one embodiment, the identifier-obtaining component and the station identifier together define an interaction region relative to the station identifier in which the hygiene monitoring device is able, using the identifier-obtaining component, to obtain the identifier from the station identifier. The interaction region is within the station. In one embodiment, the interaction region is substantially wholly within the station.

With such configurations, the identifier-obtaining component and the station identifier can only interact within a localised region relative to the station identifier. Accordingly, unintentional assignment of an identifier to an incorrect hygiene monitoring device is less likely to occur, for example, due to a caregiver passing at a distance from the station with a hygiene monitoring device.

In one embodiment, the securing component defines a cavity for receiving at least a portion of the housing. The interaction region is within the cavity. In one embodiment, the interaction region is substantially wholly within the cavity.

With such configurations, as the interaction region is within the cavity, the identifier-obtaining component can only obtain the identifier when the housing is correctly received within the cavity.

Hence, with such configurations, it is possible to further reduce the chances of an unintentional assignment, for example, when a caregiver is close by, perhaps with multiple monitoring devices.

In one embodiment, the station defines an enclosure for receiving the hygiene monitoring device. In one embodiment, the securing component of the station is within the enclosure.

In one embodiment, the station identifier comprises a transmitter configured to transmit the identifier to the identifier-obtaining component.

In one embodiment, the securing component defines a cavity for receiving at least a portion of the housing, and wherein the transmitter is directed into the cavity.

With such a configuration, it is possible to reduce the chances of an unintentional assignment.

Throughout this disclosure, the term "transmitter" may include the source of the transmission and any guiding elements (such as shields) or reflectors which are configured to guide the transmission.

In one embodiment, the transmitter is arranged to transmit the identifier preferentially into the cavity. In one embodiment, the transmitter is arranged to transmit the identifier exclusively into the cavity.

In one embodiment, the transmitter is directed to transmit towards a first wall of the cavity.

Throughout this disclosure, "transmit towards" refers to a transmission that is directed or localised towards a particular region. For example, the transmission may be a collimated beam.

In one embodiment, the transmitter is arranged to transmit from a second wall of the cavity towards the first wall. In one embodiment, the first wall comprises a shield configured to absorb or scatter the transmission from the transmitter.

In one embodiment, the first wall is opposite to the second wall.

In one embodiment, the housing is configured to be received between the first wall and the second wall. In one embodiment, the identifier-obtaining component is configured to be received between the first wall and the second wall.

In one embodiment, the securing component defines a cavity for receiving at least a portion of the housing. The cavity has a top opening. The housing is insertable through the top opening so as to be received in the cavity.

In one embodiment, the station identifier comprises a transmitter configured to transmit the identifier to the identifier-obtaining component. In one embodiment, the transmitter is configured to transmit continuously the identifier. In another embodiment, the transmitter is configured to transmit selectively the identifier when the housing is received by the securing component.

In one embodiment, the identifier-obtaining component is a photodiode. In one embodiment, the photodiode is an infrared photodiode.

In one embodiment, station identifier comprises transmitter having an LED. In one embodiment, the LED is an infrared LED.

In one embodiment, the identifier-obtaining component and the station identifier are configured to interact wirelessly, optionally using a standardised short-range wireless protocol such as Bluetooth, Zigbee or IrDA.

In one embodiment, the identifier-obtaining component and the station identifier are configured to interact via near field communication (NFC) and/or radio-frequency identification (RFID).

In one embodiment, the hygiene monitoring device comprises a transmitter configured to transmit data to an external device, for example, a centralised server. In one embodiment, the hygiene monitoring device is configured to transmit the identifier and/or information relating to the monitored data.

In one embodiment, the hygiene monitoring device is configured to simultaneously transmit the identifier and the information relating to the monitored data to the external device.

In one embodiment, the identifier-obtaining component comprises a memory for storing the identifier.

In one embodiment, the station identifier comprises a memory to store the identifier.

In one embodiment, the hygiene monitoring device comprises a battery. The station is configured to charge the battery when the hygiene monitoring device is received in the station.

In one embodiment, the station is a charging station for the hygiene monitoring device.

In one embodiment, hygiene monitoring device is configured to monitor wetness level, a temperature, a presence of an analyte and/or a concentration of a particular substance (liquid or gas) associated with the user.

In one embodiment, the hygiene monitoring device comprises a biosensor.

In one embodiment, the hygiene monitoring device is removably attachable to a wearable hygiene article. In one embodiment, the hygiene monitoring device comprises a mechanical fastener component, such as a hook material patch, that may removably attach to a corresponding loop material on the wearable hygiene article. In one embodiment, the hygiene monitoring device comprises an adhesive fastener component, such as a pressure sensitive adhesive, that may removably attach to a corresponding tape landing zone on the wearable hygiene article.

In one embodiment, the wearable hygiene article is a disposable absorbent article, such as a diaper or incontinence shield.

In one embodiment, the hygiene monitoring device is configured to be removably attached to a hygiene product, preferably a disposable absorbent hygiene product.

In one embodiment, the hygiene monitoring device is removably attachable to an outer surface of the hygiene product.

In one embodiment, the hygiene monitoring device is configured to store the identifier. In one embodiment, the hygiene monitoring device is configured to transmit the identifier together with any sensed data.

In one embodiment, the hygiene monitoring device is re-useable.

In one embodiment, the hygiene monitoring device comprises a cell.

In one embodiment, the hygiene monitoring device is rechargeable.

In one embodiment, the hygiene monitoring device comprises a replaceable cell.

In one embodiment, the hygiene monitoring device is disposable.

In one embodiment, the hygiene monitoring system further comprises a server for receiving data transmitted by the hygiene monitoring device. In one embodiment, the server is programmable to include an association of the identifier with a particular resident.

In one embodiment, the hygiene monitoring system further comprises a wearable article. In one embodiment, the hygiene monitoring device is removably attachable to the wearable article.

In another aspect of the present disclosure, there is provided a hygiene monitoring device. The hygiene monitoring device comprises a housing configured to be received and held in a securing component of a station. The hygiene monitoring device comprises an identifier-obtaining component configured to receive, when in use, an identifier from the station when the housing of the hygiene monitoring device is received by the securing component of the station.

The hygiene monitoring device of this aspect of the present disclosure may optionally have any of the features, or any combination of the features, of any of the hygiene monitoring devices disclosed herein.

In another aspect of the present disclosure, there is provided a station for receiving a hygiene monitoring device. The station comprises a securing component configured to receive and hold a housing of the hygiene monitoring device at a defined location relative to the station. The station comprises a station identifier configured to provide an identifier to an identifier-obtaining component of the hygiene monitoring device when the housing of the hygiene monitoring device is received by the securing component of the station.

The station of this aspect of the present disclosure may optionally have any of the features, or any combination of the features, of any of the stations disclosed herein.

BRIEF DESCRIPTION OF THE DRAWINGS

For a better understanding of the present disclosure and to show how the same may be carried into effect, reference will now be made, by way of example only, to the accompanying drawings, in which.

DETAILED DESCRIPTION OF THE INVENTION

Figure 1:
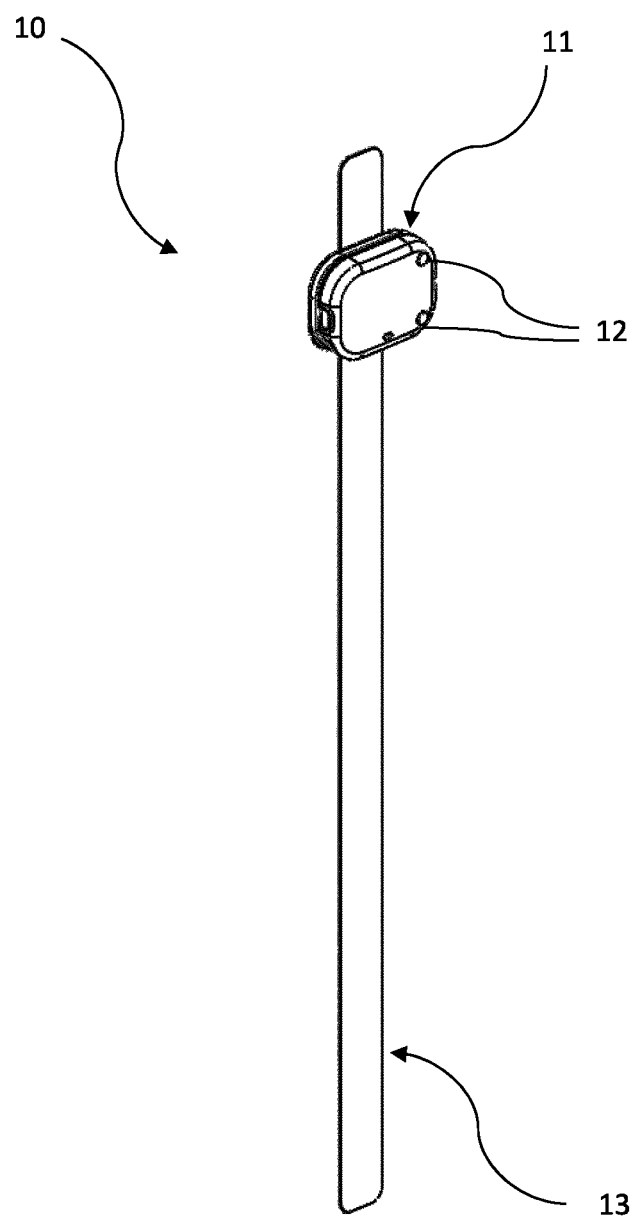
FIGS. 1 and 2 show a hygiene monitoring device for monitoring a hygienic state of a user.

FIG. 1 shows a hygiene monitoring device 10 for monitoring a hygienic state of a user. The hygiene monitoring device 10 may be removably attached to a wearable article of a user so that it may monitor the hygienic state of the article.

The hygiene monitoring device 10 comprises a housing 11 and an electrode strip 13 which extends from the housing 11. As shown in FIG. 1, the electrode strip 13 extends on both sides of the housing 11. In other embodiments, the electrode strip 13 may extend on only one side of the housing 11.

The housing 11 has an identifier-obtaining component 12 comprising two spaced-apart photodiodes. The identifier-obtaining component 12 is for obtaining an identifier from the station identifier 22 of the station 20 (as detailed below). The identifier-obtaining component 12 further comprises memory which is configured to store the identifier received from the station identifier 22 of the station 20.

The hygiene monitoring device 10 further comprises a transmitter (not shown) which is configured to transmit data to an external device, such as a centralised server (not shown). The hygiene monitoring device 10 is configured to transmit the stored identifier together with information relating to the monitored hygienic state of the article.

Figure 2:
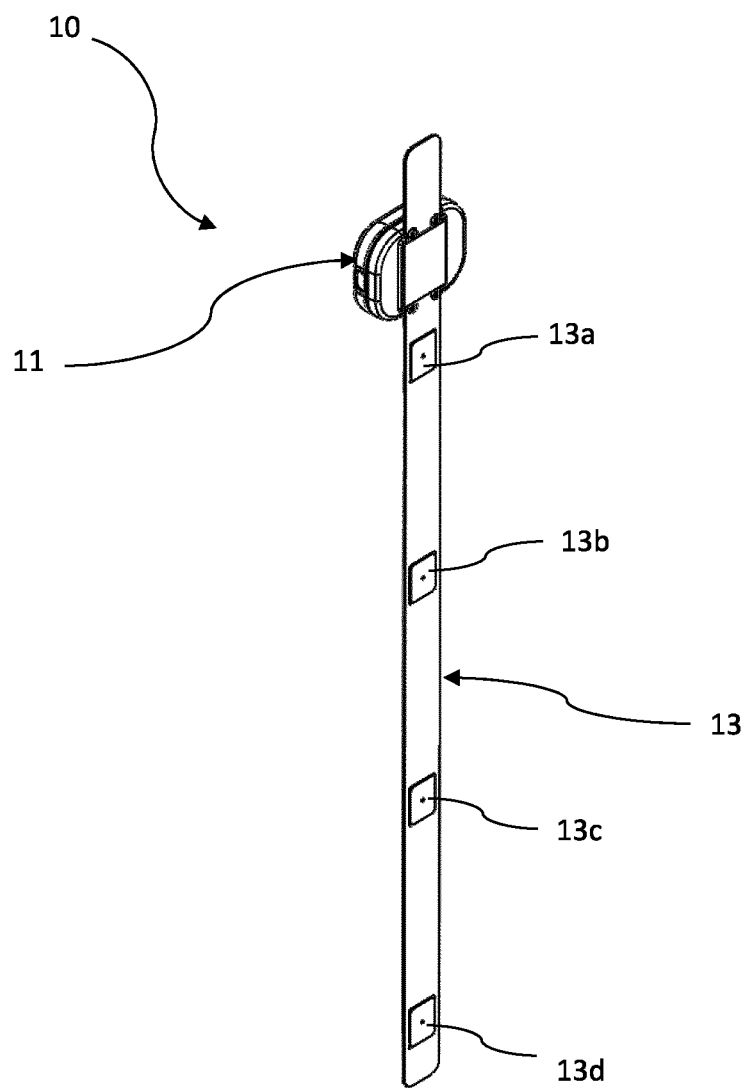
Figure 3:
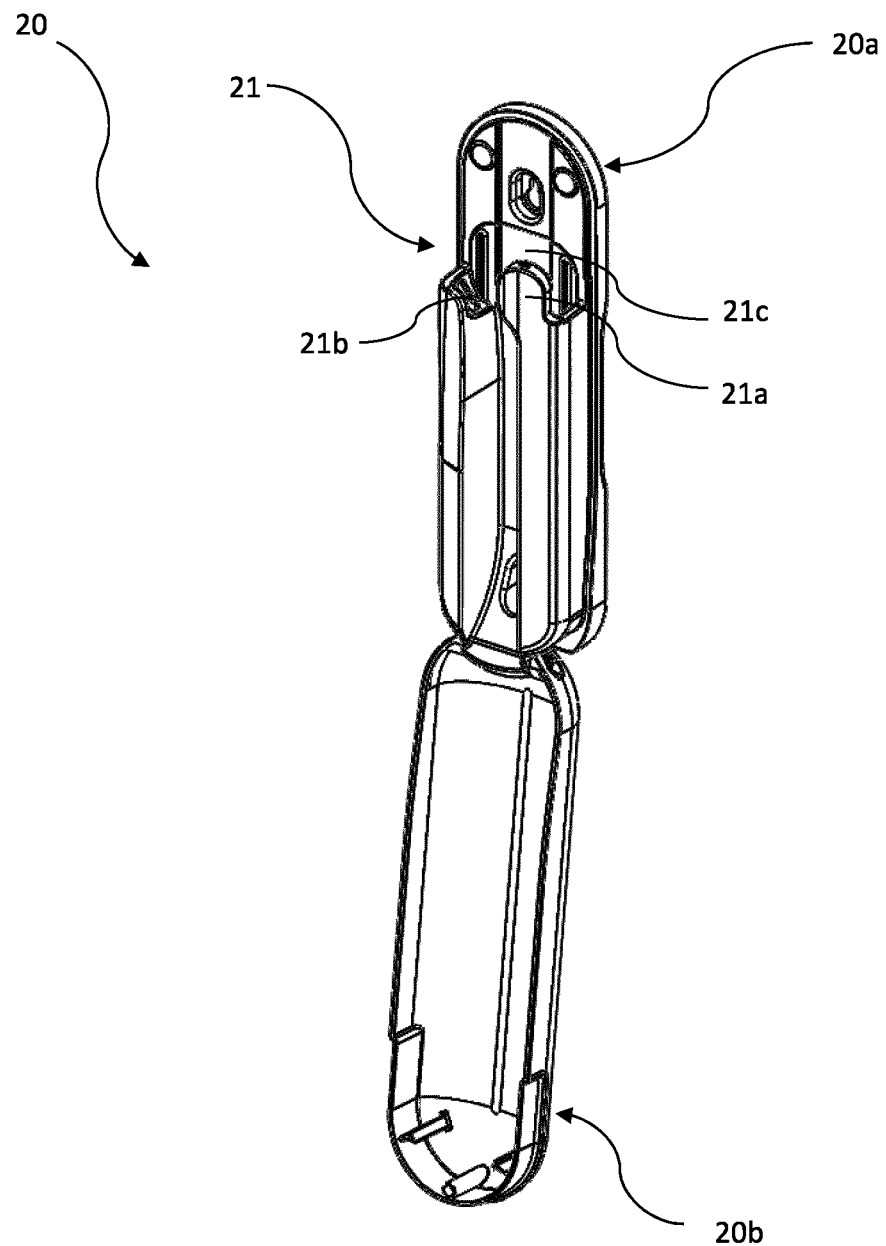
FIGS. 3 to 8 show a station for receiving the hygiene monitoring device shown in FIGS. 1 and 2.
Figure 4:
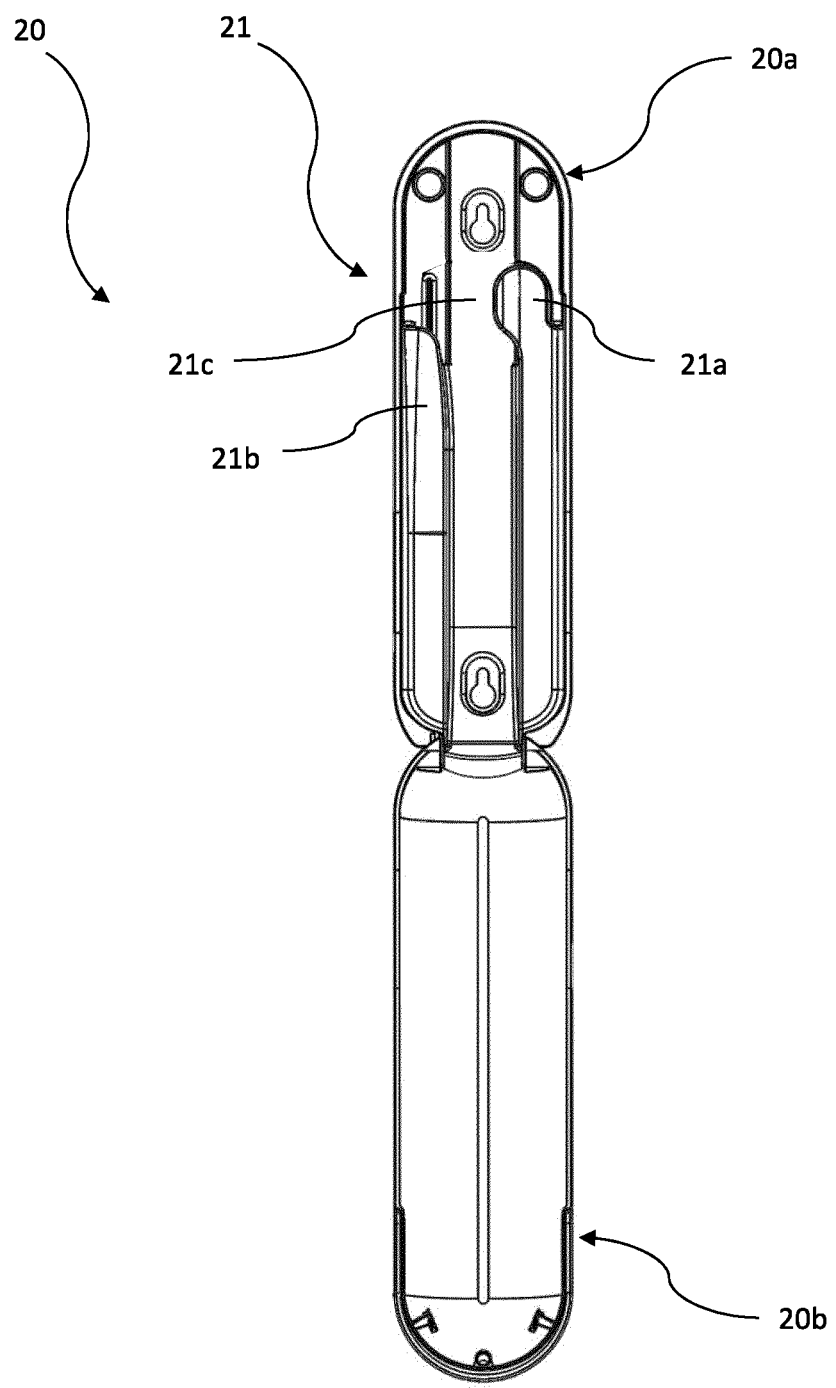

As shown in FIG. 2, the electrode strip 13 of the hygiene monitoring device 10 comprises four electrodes 13a-13d which are spaced apart along the longitudinal length of the electrode strip 13. The hygiene monitoring device 10 is configured such that the electrodes 13a-13d may be brought into contact with the wearable article such that they may measure the hygienic state of the article, for example, by measurement of the wetness level of the article, presence of particular chemical compounds/compositions and/or pH levels. The specific arrangements of the electrodes will be known to a person skilled in the art, and, for example, may include any of the arrangements disclosed in WO 2016/090492, the contents of which are hereby incorporated by reference to the extent permitted by law.

FIGS. 3 to 8 show a station 20 for receiving the hygiene monitoring device 10. The station 20 comprises a first casing portion 20a and a second casing portion 20b. The second casing portion 20b is pivotable relative to the first casing portion 20a so as to open and close the station 20.

The station 20 comprises a securing component 21 which is configured to receive and hold the housing 11 of the hygiene monitoring device 10 at a defined location relative to the station 20.

Figure 5:
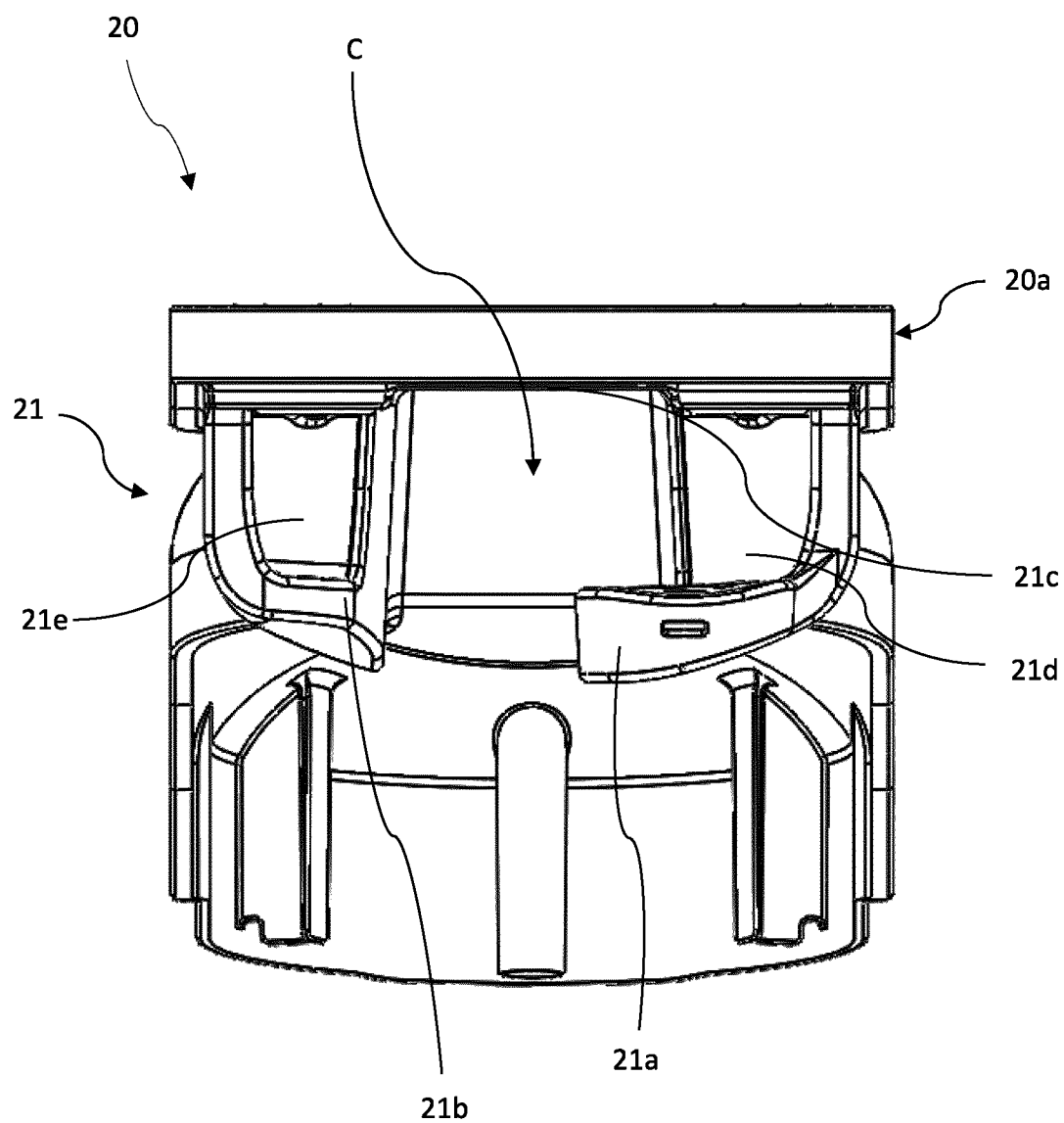
Figure 6:
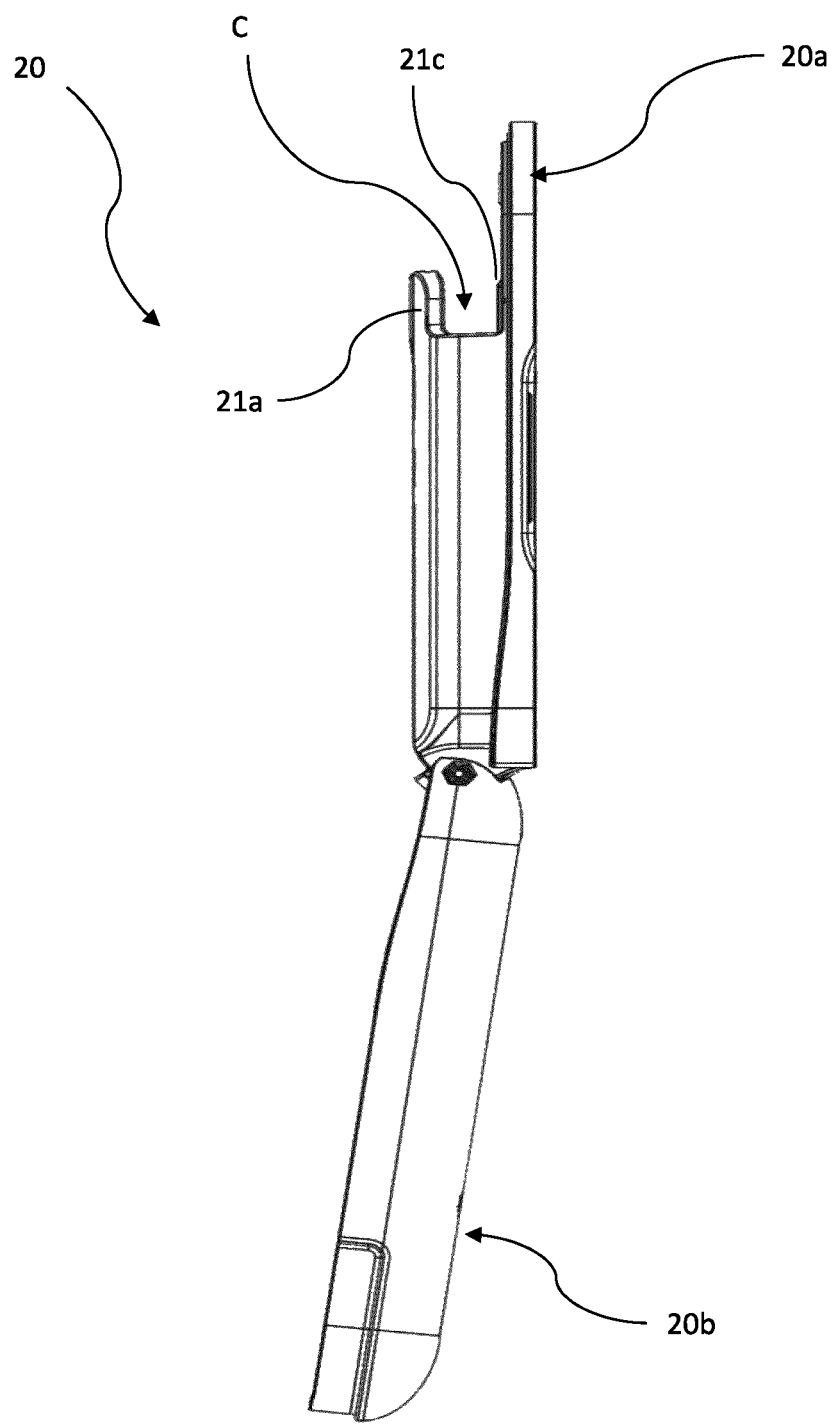

As can be seen from FIG. 5, the securing component 21 comprises a first flange 21a, a second flange 21b, a back wall 21c, a first shelf 21d and a second shelf 21e. The first shelf 21d corresponds to the first flange 21a and the second shelf 21e corresponds to the second flange 21b. The securing component 21 defines a cavity C delimited by the first flange 21a, the second flange 21b, the back wall 21c, the first shelf 21d and the second shelf 21e.

The hygiene monitoring device 10 may be received in the station 20 by inserting the housing 11 into the cavity C defined by the securing component 21. Once the housing 11 is inserted, the securing component 21 holds the housing 11 in place such that the hygiene monitoring device 10 is held at a defined location relative to the station.

Figure 7:
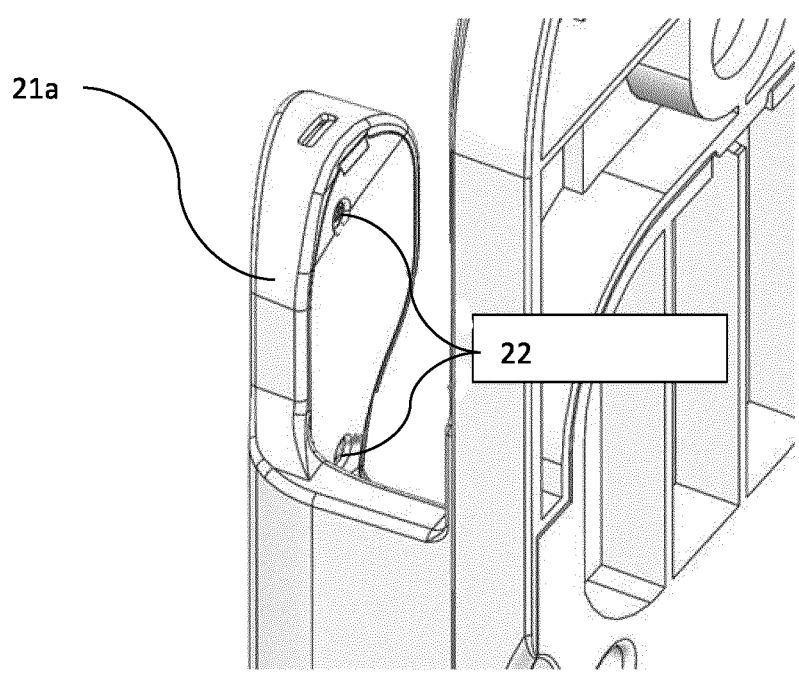

As can be seen in FIG. 7, the first flange 21a of the securing component 21 has a station identifier 22 comprising two spaced-apart LEDs which act as transmitters. The LEDs of the station identifier 22 are arranged to face the back wall 21c of the securing component 21. In other words, the LEDs of the station identifier 22 are arranged to transmit into the cavity C of the securing component 21 and towards the back wall 21c. Using this arrangement, relatively little light escapes the cavity C of the securing component 21. The LEDs of the station identifier 22 are arranged to align with the photodiodes of the identifier-obtaining component 12 when the housing 11 is received in the securing component 21, such that the identifier-obtaining component 12 and the station identifier 22 may interact.

The station identifier 22 is configured to store an identifier which is associated with the station 20. For example, the identifier may be any sort of code, such as a numeric or alphanumeric code. As used herein, the term 'identifier' refers to any information which allows for the station identifier 22 to be identified and differentiated from other station identifiers. For example, 'identifier' also refers to any manipulated (e.g., encrypted, hashed, signed or otherwise processed) version of the stored identifier.

As detailed further below, the station identifier 22 is configured to transmit the identifier using the LEDs to the identifier-obtaining component 12 when the housing 11 is received in the securing component 21.

Figure 8:
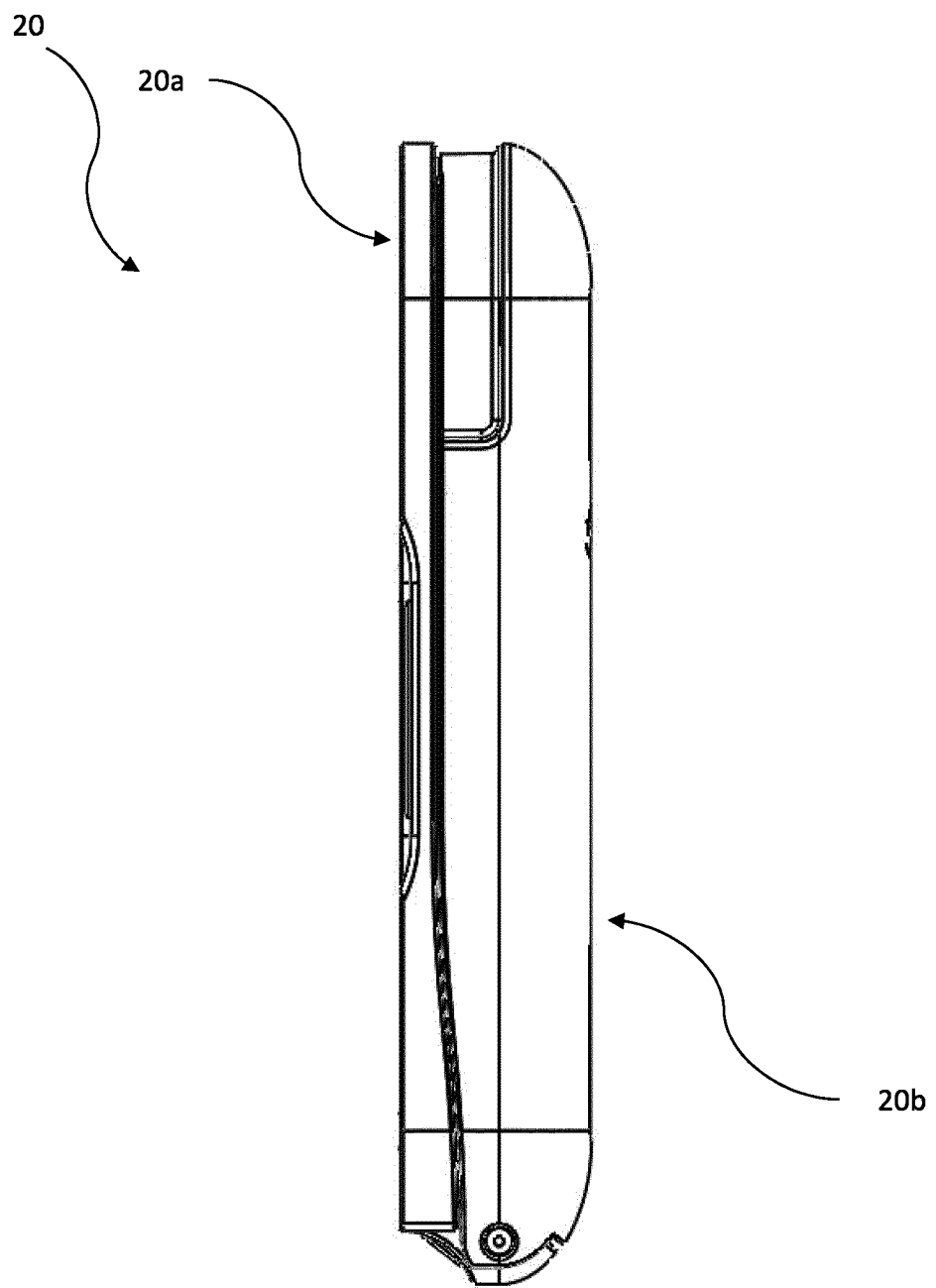

FIG. 8 shows the station 20 in a closed configuration in which the first casing portion 20a and the second casing portion 20b together define an enclosure suitable for receiving the hygiene monitoring device 10 therein.

Figure 9:
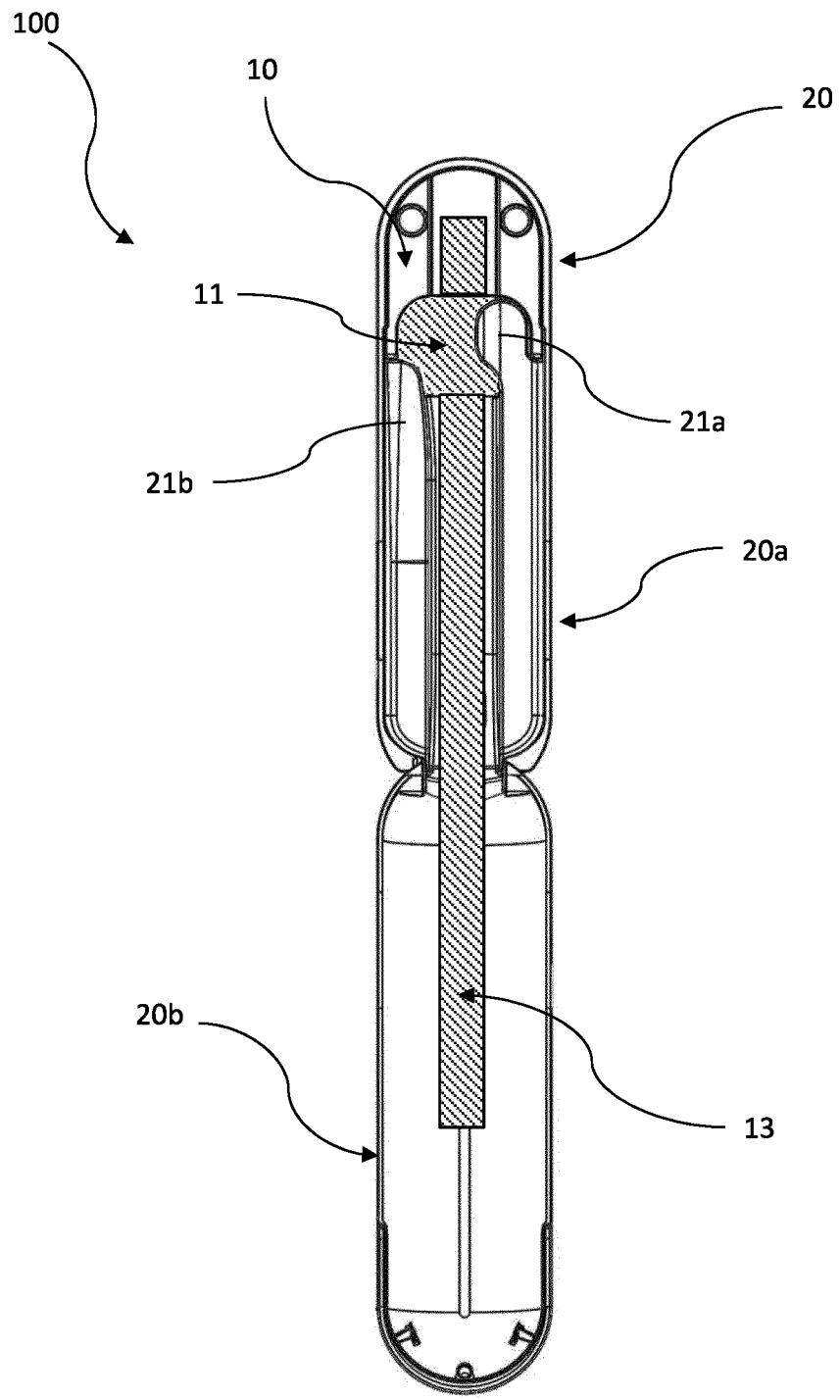
FIGS. 9 to 11 show a hygiene monitoring system comprising the hygiene monitoring device shown in FIGS. 1 and 2, and the station shown in FIGS. 3 to 8.
Figure 10:
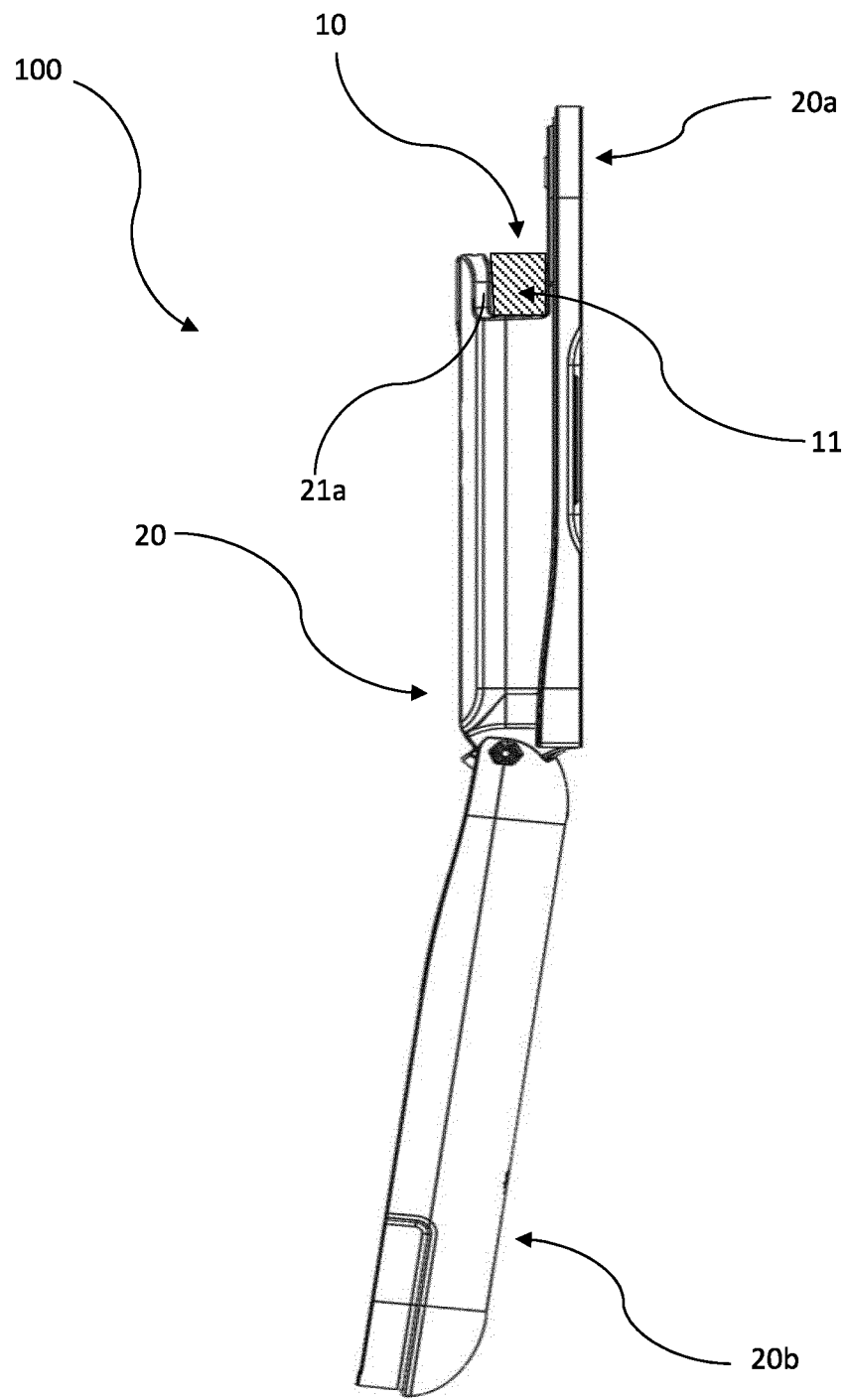
Figure 11:
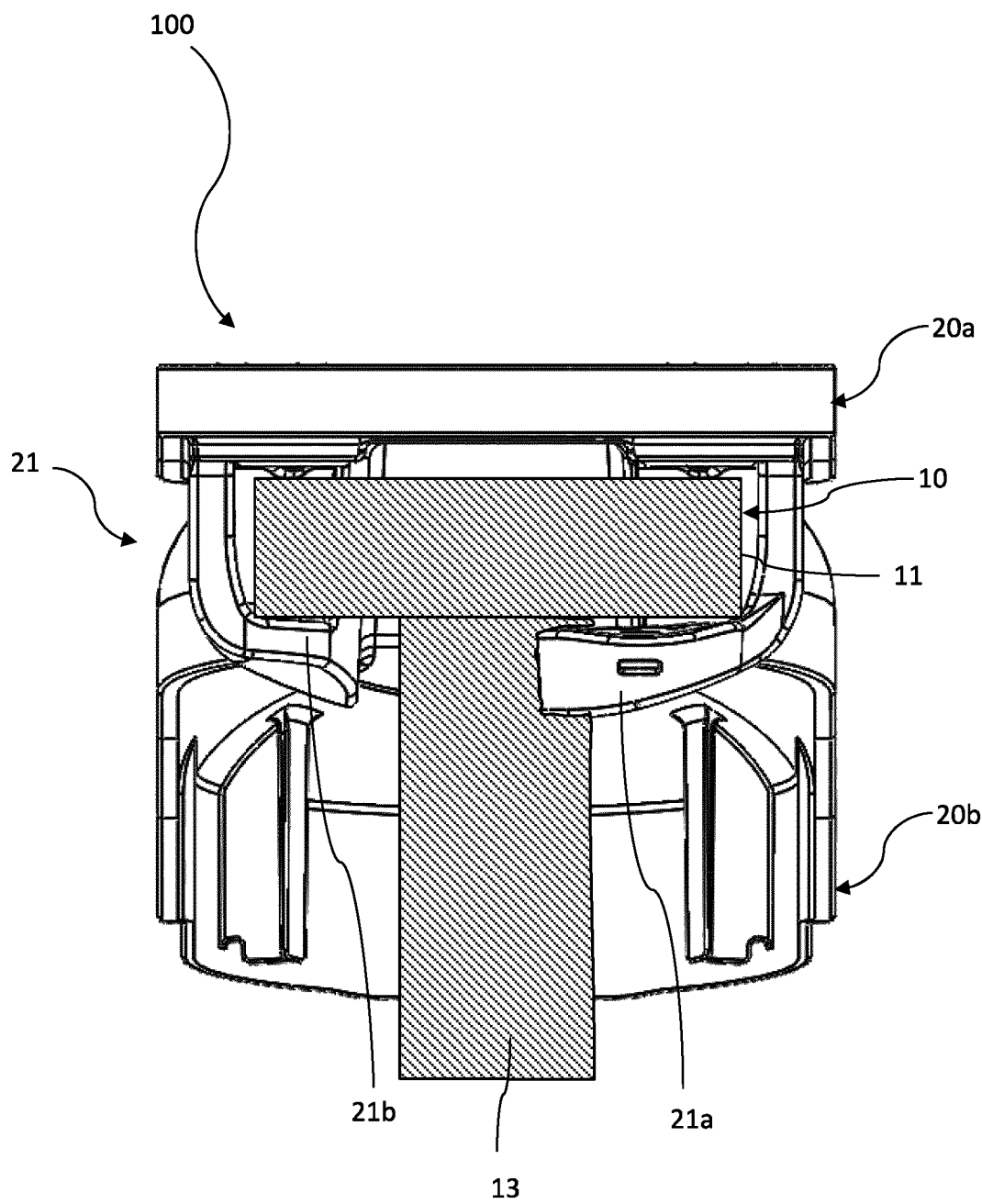

FIGS. 9 to 11 show a hygiene monitoring system 100 comprising the hygiene monitoring device 10 and the station 20. FIGS. 9 to 11 show the hygiene monitoring device 10 received in the station 20. As can be seen, the securing component 21 receives and holds the housing 11 of the hygiene monitoring device such that the housing 11 is held at a defined location relative to the station 20. The electrode strip 13 is not directly held by the securing component 21 and extends relatively freely above and below the housing 11.

The hygiene monitoring device 10 may be inserted into the station 20 by inserting the housing 11 into the securing component 21. In particular, the cavity C has a top opening through which the housing 11 may be inserted downwardly. The first shelf 21d and the second shelf 21e act to limit the housing 11 from further downward translation.

Once the hygiene monitoring device 10 is received in the station 20 as shown in FIGS. 9 to 11, the second housing portion 20b may be pivoted relative to the first housing portion 20a so as to close the station 20. Upon closing the station 20 whilst the hygiene monitoring device 10 is received therein, the electrode strip 13 bends to form a U shape.

Once the housing 11 is correctly received in the securing component 21, the LEDs of the station identifier 22 are arranged to align with the photodiodes of the identifier-obtaining component 12 so that the station identifier 22 is able to transmit the stored identifier to the identifier-obtaining component 12. However, if the housing 11 is not correctly received in the securing component 21 (for example, not fully inserted), due to the arrangement of the LEDs of the station identifier 22, the identifier-obtaining component 12 will not be able to receive the identifier of the station identifier 22.

In other words, the identifier-obtaining component 12 and the station identifier 22 define an interaction region which is a volume (which may be defined relative to the station 20) in which the identifier-obtaining component 12 is able to receive the identifier from the station identifier 22. Outside this interaction region, the identifier-obtaining component 12 cannot receive the identifier from the station identifier 22. In this particular embodiment, the interaction region is substantially within the cavity C of the securing component 21, and, in particular, the volume immediately proximal to the LEDs of the station identifier 22.

Below, the use of the hygiene monitoring system 100 is described in detail, and, in particular, the assignment of the hygiene monitoring device 10 to the station 20.

After use of known hygiene monitoring devices, they may be stored overnight (or during the day, depending on the particular use), for example, after washing the device. It has been found that after use, caregivers tend to store the hygiene monitoring devices in close proximity to the resident to which the hygiene monitoring device is to be associated with, such as close to the resident's bed.

With the hygiene monitoring system 100, the station 20 may be placed within the care home (permanently or semi-permanently), for example, by fixing it to a wall or other stationary element of the care home) so that it is associated with a particular resident, for example, by placing it on the wall next to their bed. Accordingly, the identifier stored by the station identifier 22 is associated with a particular resident. The external device (e.g., a centralised server) to which the hygiene monitoring device 10 transmits to may be updated to store that this particular identifier is associated with this particular resident.

Using the hygiene monitoring system 100, the caregiver may conveniently place the hygiene monitoring device 10 in the station 20 regularly before/after its use. As the station identifier 22 is then associated with the particular bed (which is in turn associated with a particular patient), upon the identifier-obtaining component 12 receiving the identifier, the hygiene monitoring device 10 may store (in the identifier-obtaining component's memory) and transmit/upload the identifier which is associated with the station 20, which, in turn is associated with a bed, which, in turn is associated with a particular resident. Therefore, the external device (e.g., a centralised server) to which the hygiene monitoring device 10 transmits to will be able to associate the received data with a particular resident and may therefore be configured to alert a caregiver to which resident needs attention.

The hygiene monitoring system 100 may comprise multiple stations 20 each associated with a particular resident. The external device (e.g., a centralised server) to which the hygiene monitoring device 10 transmits to may be updated to store which identifier of each station 20 is associated with which of the particular residents.

If the hygiene monitoring device 10 is to be used with a different resident, the caregiver simply correctly places it in the station 20 associated with a particular resident such that the hygiene monitoring device 10 receives and stores a new identifier received from the station identifier 22, and transmits this new identifier to the external device so that the external device can associate the hygiene monitoring device 10 with the new resident.

Although the above explanation is considered to fully clarify how the present disclosure may straightforwardly be put into effect by those skilled in the art, it is to be regarded as purely exemplary.

For example, although the above embodiment of the hygiene monitoring system 100 includes a station identifier 22 and an identifier-obtaining component 12 which interact using LEDs, other means of interaction are conceived so long as the station identifier is able to provide an identifier to the identifier-obtaining component when the housing the hygiene monitoring device is received by the securing component of the station. For example, the identifier-obtaining component and the station identifier may be configured to interact via near field communication (NFC), electrical connections (e.g., using contact pins), physical or optical connections.

Furthermore, the interaction region of the station identifier and the identifier-obtaining component need not be wholly within the securing component. In other embodiments, the interaction region is in proximity to the station, and, optionally, within the station.

In the above embodiment, the hygiene monitoring device 10 is configured to transmit data to an external device such as a centralised server. However, in alternative embodiments, the hygiene monitoring device may be configured to store the identifier and the monitored information and upload this data at a later time during, for example, a cable upload to a personal computer.

Even though the above embodiment of the hygiene monitoring device 10 comprises an electrode strip 13 for monitoring the hygienic state of the article, alternative embodiments are contemplated. For example, the hygiene monitoring device may comprise any type of sensor, such as a biosensor and/or temperature sensor configured to monitor the hygienic state of the article.

In the above embodiment, the hygiene monitoring device 10 transmits the identifier received from the station 20. In certain embodiments, the hygiene monitoring device 10 transmits the identifier received from the station 20 together with a hygiene monitoring device identifier. In this embodiment, the central device (such as a server) receiving transmissions from the hygiene monitoring device 10 may associate the identifier received from the station 20 with the hygiene monitoring device identifier such that during future transmissions, the hygiene monitoring device 10 may only transmit the hygiene monitoring device identifier.

Even though in the above embodiment, the identifier-obtaining component 12 comprises two spaced-apart photodiodes and the station identifier 22 comprises two spaced-apart LEDs, and number of photodiodes and LEDs may be used. For example, the identifier-obtaining component may comprise one photodiode and the station identifier may comprise one LED.

In certain embodiments, identifier-obtaining component comprises a photodiode and an LED, and the station identifier comprises a photodiode and an LED configured such that the identifier-obtaining component and station identifier may bi-directionally communicate with each other. Optionally, the station device is configured to verify whether the identifier-obtaining component correctly obtained and/or stored the identifier.

Even though the above has been described in relation to use in a care home, the above system is suitable for use in any institution/location, such as a hospital or nursery.

All of the above are fully in the scope of the disclosure and are considered to form the basis for alternative embodiments in which one or more combinations of the above-described features are applied, without limitation to the specific combinations disclosed above.

In light of this, there will be many alternatives which implement the teaching of the present disclosure. It is expected that one skilled in the art will be able to modify and adapt the above disclosure to suit their own circumstances and requirements within the scope of the present disclosure, while retaining some or all technical effects of the same, either disclosed or derivable from the above, in light of his common general knowledge in this art. All such equivalent modifications or adaptations fall within the scope of the present invention as defined by the appended claims.

What is claimed is:

1. A hygiene monitoring system, comprising:
   a hygiene monitoring device, the hygiene monitoring device comprising a housing with an identifier-obtaining component; and
   a station for receiving the hygiene monitoring device, the station comprising:
   a securing component configured to receive and hold the housing at a defined location relative to the station; and
   a station identifier configured to provide an identifier to the identifier-obtaining component when the housing of the hygiene monitoring device is received by the securing component of the station.

2. The hygiene monitoring system of claim 1, wherein the identifier-obtaining component and the station identifier together define an interaction region relative to the station identifier in which the hygiene monitoring device is able, using the identifier-obtaining component, to obtain the identifier from the station identifier, and wherein the interaction region is within the station.

3. The hygiene monitoring system of claim 2, wherein the securing component defines a cavity for receiving at least a portion of the housing, and wherein the interaction region is within the cavity.

4. The hygiene monitoring system of claim 1, wherein the station identifier comprises a transmitter configured to transmit the identifier to the identifier-obtaining component.

5. The hygiene monitoring system of claim 4, wherein the securing component defines a cavity for receiving at least a portion of the housing, and wherein the transmitter is directed into the cavity.

6. The hygiene monitoring system of claim 5, wherein the transmitter is directed to transmit towards a first wall of the cavity.

7. The hygiene monitoring system of claim 6, wherein the transmitter is arranged to transmit from a second wall of the cavity towards the first wall.

8. The hygiene monitoring system of claim 7, wherein the first wall is opposite to the second wall.

9. The hygiene monitoring system of claim 1, wherein the securing component defines a cavity for receiving at least a portion of the housing, and wherein the cavity has a top opening, and wherein the housing is insertable through the top opening so as to be received in the cavity.

10. The hygiene monitoring system of claim 1, wherein the station identifier comprises a transmitter configured to transmit the identifier to the identifier-obtaining component, and further wherein the transmitter is configured to transmit continuously the identifier or the transmitter is configured to transmit selectively the identifier when the housing is received by the securing component.

11. The hygiene monitoring system of claim 1, wherein the identifier-obtaining component is a photodiode.

12. The hygiene monitoring system of claim 1, wherein the station identifier comprises transmitter having an LED.

13. The hygiene monitoring system of claim 1, wherein the identifier-obtaining component and the station identifier are configured to interact wirelessly.

14. The hygiene monitoring system of claim 1, wherein the hygiene monitoring device comprises a battery, and wherein the station is configured to charge the battery when the hygiene monitoring device is received in the station.

15. The hygiene monitoring system of claim 1, wherein the hygiene monitoring device is configured to monitor wetness.

16. The hygiene monitoring system of claim 1, wherein the hygiene monitoring device is configured to be removably attached to a hygiene product.

17. The hygiene monitoring system according to claim 16, wherein the hygiene monitoring device is removably attachable to an outer surface of the hygiene product.

18. The hygiene monitoring system of claim 2, wherein the interaction region is wholly within the station.

19. The hygiene monitoring system of claim 3, wherein the interaction region is wholly within the cavity.

20. The hygiene monitoring system of claim 11, wherein the photodiode is an infrared photodiode.

21. The hygiene monitoring system of claim 12, wherein the LED is an infrared LED.

22. The hygiene monitoring system of claim 16, wherein said hygiene product is a disposable absorbent hygiene product.

* * * * *